United States Patent [19]

Buckler et al.

[11] 3,948,932
[45] Apr. 6, 1976

[54] PHENYL- AND (SUBSTITUTED)-PHENYL-1,2,3-TRIAZOLE-ALKANOIC AND -ALKENOIC ACIDS

[75] Inventors: Robert Thomas Buckler, Edwardsburg, Mich.; Harold Eugene Hartzler, Elkhart, Ind.; Shin Hayao, Tokyo, Japan; Gust Nichols, Elkhart, Ind.

[73] Assignee: Miles Laboratories, Inc., Elkhart, Ind.

[22] Filed: Oct. 18, 1974

[21] Appl. No.: 515,974

Related U.S. Application Data

[62] Division of Ser. No. 364,609, May 29, 1973.

[52] U.S. Cl................................ 260/308 A; 424/244
[51] Int. Cl.$^2$........................................ C07D 249/06
[58] Field of Search................................ 260/308 A

[56] References Cited
OTHER PUBLICATIONS

Collier et al., Chem. Abstracts, Vol. 56, Column 5943 (1962).
Tanaka et al., J. Org. Chem., Vol. 38, pp. 2708–2712, (1973).

Primary Examiner—Alton D. Rollins
Attorney, Agent, or Firm—Myron B. Sokolowski

[57] ABSTRACT

Certain phenyl- and (substituted)-phenyl-1,2,3-triazole-alkanoic and -alkenoic acids exhibit antiinflammatory or antipyretic activity.

12 Claims, No Drawings

PHENYL- AND (SUBSTITUTED)-PHENYL-1,2,3-TRIAZOLE-ALKANOIC AND -ALKENOIC ACIDS

This is a division of application Ser. No. 364,609, filed May 29, 1973.

SUMMARY OF THE INVENTION

The chemical compounds of this invention are represented by general structural Formula I:

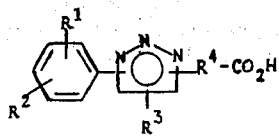
(I)

In Formula I, $R^1$ and $R^2$ independently are hydrogen, loweralkyl, loweralkoxy, amino, loweralkylamino, lower -alkylamido, or halogeno; $R^3$ is hydrogen, loweralkyl, loweralkanoyl, or phenyl; $R^4$ is a —CH$_2$—, —CH$_2$—CH$_2$—, —CH$_2$—CH$_2$—CH$_2$—, or a —CH=CH— radical; and

represents the triazole structures

Furthermore, the prefix lower- as applied to appropriate groups of $R^1$, $R^2$ and $R^3$ means one to three carbon atoms. By definition, the atoms in the triazole ring are numbered in a counterclockwise manner with the nitrogen atom on the right side of the ring designated as (1), as in Formula II:

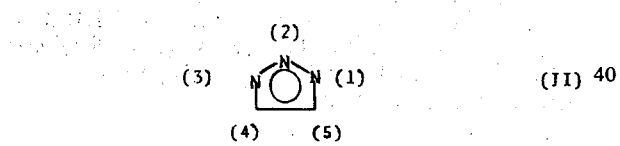
(II)

Because Formula I is asymmetrical, there are five preferred arrangements of the ($R^1$,$R^2$)-phenyl and the loweralkanoic acid loweralkenoic acid substituents $R^4$-CO$_2$H around the triazole ring when $R^3$ is hydrogen. These preferred configurations are represented by Formulas III through VII respectively:

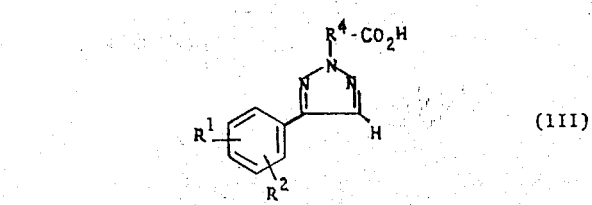
(III)

4-($R^1$,$R^2$)-phenyl-1,2,3,(2H)-triazole-2-($R^4$-CO$_2$H);

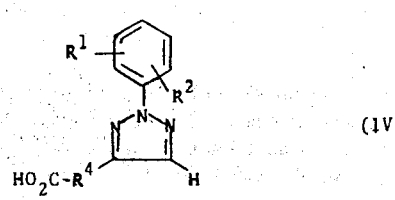
(IV)

2-($R^1$,$R^2$)-phenyl-1,2,3,(2H)-triazole-4-($R^4$-CO$_2$H);

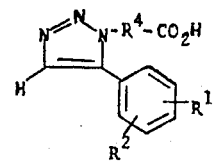
(V)

5-($R^1$,$R^2$)-phenyl-1,2,3,(1H)-triazole-1-($R^4$-CO$_2$H);

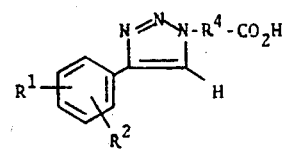
(VI)

4-($R^1$,$R^2$)-phenyl-1,2,3,(1H)-triazole-1-($R^4$-CO$_2$H); and,

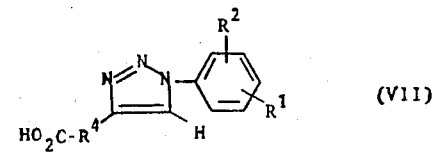
(VII)

1-($R^1$,$R^2$)-phenyl-1,2,3,(1H)-triazole-4-($R^4$-CO$_2$H).

When $R^3$ is other than hydrogen in Formula I, the following represent preferred configurations thereof:

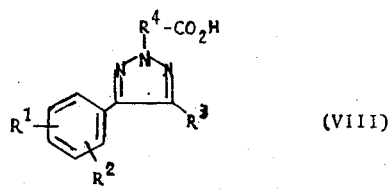
(VIII)

5-$R^3$-4-($R^1$,$R^2$)-phenyl-1,2,3,(2H)-triazole-2-($R^4$-CO$_2$H);

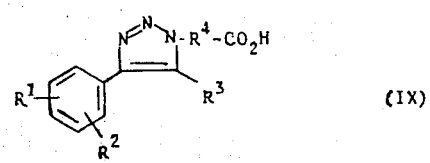
(IX)

5-$R^3$-4-($R^1$, $R^2$)-phenyl-1,2,3,(1H)-triazole-1-($R^4$-CO$_2$H); and

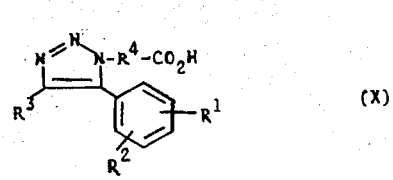
(X)

5-($R^1$,$R^2$)-phenyl-4-$R^3$-1,2,3,(1H)-triazole-1-($R^4$-CO$_2$H).

The following specific compounds comprise preferred embodiments of general Formula I:

1. [4-phenyl-1,2,3,(2H)-triazole-2]-acetic acid;

2. 3-[4-phenyl-1,2,3,(2H)-triazole-2]-propionic acid;
3. 4-[4-phenyl-1,2,3,(2H)-triazole-2]-butyric acid;
4. 3-[4-(m-chloro)-phenyl-1,2,3,(2H)triazole-2]-propionic acid;
5. 3-[4-(m-bromo)-phenyl-1,2,3,(2H)-triazole-2]-propionic acid;
6. 3-[4-(m-methyl)-phenyl-1,2,3,(2H)-triazole-2]-propionic acid;
7. 3-[4-(3,5-dichloro)-phenyl-1,2,3,(2H)triazole-2]-propionic acid;
8. 3-[4-(m-acetamido)-phenyl-1,2,3,(2H)-triazole-2]-propionic acid;
9. 3-[2-phenyl-1,2,3,(2H)-triazole-4]-propionic acid;
10. 3-[2-(m-chloro)-phenyl-1,2,3,(2H)-triazole-4]-propionic acid;
11. 3-[2-(m-bromo)-phenyl-1,2,3,(2H)-triazole-4]-propionic acid;
12. 3-[2-phenyl-1,2,3,(2H)-triazole-4]-acrylic acid;
13. 3-[2-(m-chloro)-phenyl-1,2,3,(2H)-triazole-4]-acrylic acid;
14. 3-[2-(m-bromo)-phenyl-1,2,3,(2H)-triazole-4]-acrylic acid;
15. 3-[5-phenyl-1,2,3,(1H)-triazole-1]-propionic acid;
16. 3-[5-(m-fluoro)-phenyl-1,2,3,(1H)-triazole-1]-propionic acid;
17. [4-phenyl-1,2,3,(1H)-triazole]-1-acetic acid;
18. 3-[4-phenyl-1,2,3,(1H)-triazole-1]-propionic acid;
19. 4-[4-phneyl-1,2,3,(1H)-triazole-1]-butyric acid;
20. 3-[4-(m-chloro)-phenyl-1,2,3,(1H)-triazole-1]-propionic acid;
21. 3-[4-(m-bromo)-phenyl-1,2,3,(1H)-triazole-1]-propionic acid;
22. 3-[4-(m-fluoro)-phenyl-1,2,3,(1H)-triazole-1]-propionic acid;
23. 3-[4-(m-methyl)-phenyl-1,2,3,(1H)-triazole-1]-propionic acid;
24. 3-[4-(m-ethoxy)-phenyl-1,2,3,(1H)-triazole-1]-propionic acid;
25. 3-[4-(m-amino)-phenyl-1,2,3,(1H)-triazole-1]-propionic acid;
26. 3-[4-(m-acetamido)-phenyl-1,2,3,(1H)-triazole-1]-propionic acid;
27. 3-[1-phenyl-1,2,3,(1H)-triazole-4]-propionic acid;
28. 3-[1-(m-fluoro)-phenyl-1,2,3,(1H)-triazole-4]-propionic acid;
29. 3-[1-(m-chloro)-phenyl-1,2,3,(1H)-triazole-4]-propionic acid;
30. 3-[1-(m-fluoro)-phenyl-1,2,3,(1H)-triazole-4]-acrylic acid;
31. 3-[1-phenyl-1,2,3,(1H)-triazole-4-]-acrylic acid;
32. 3-[4-phenyl-5-methyl-1,2,3,(1H)-triazole-2]-propionic acid;
33. 3-[4-phenyl-5-acetyl-1,2,3,(1H)-triazole-2]-propionic acid;
34. 3-[4,5-diphenyl-1,2,3,(1H)-triazole-2]-propionic acid; and
35. 3-[4,5-diphenyl-1,2,3,(2H)-triazole-1-]-propionic acid.

The compounds listed above are also preferred embodiments of the Formulas III tthrough IX. Table I correlates the specific compounds with the general Formulas. In Table I, each compound is identified by the numeral assigned above.

Table I

| Specific Compounds | General Formula |
|---|---|
| 1 thru 8 | III |
| 9 thru 14 | IV |

Table I-continued

| Specific Compounds | General Formula |
|---|---|
| 15 and 16 | V |
| 17 thru 26 | VI |
| 27 thru 31 | VII |
| 32 thru 34 | VIII |
| 35 | IX, X |

Compounds having the configuration represented by Formulas V and VI are synthesized by the thermal addition of $(R^1,R^2)$-phenylacetylenes to azido acids (J. A. Durden, Jr., et al., J. Chem. Eng. Data, 9: 228 [1964]):

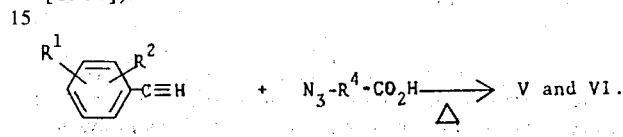

The mixture of isomers obtained from this reaction can be separated by fractional crystallization or by chromatography of the corresponding methyl esters on silicic acid. The methyl esters can easily be reconverted into the free acids.

Compounds with structures corresponding to Formulas III and VI are formed when 4-$(R^1,R^2)$-phenyltriazoles are alkylated with aliphatic acids which contain an appropriate leaving group, X:

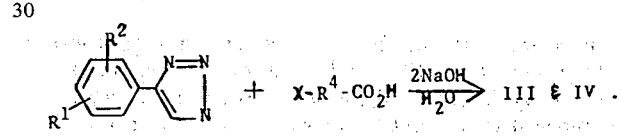

Isomers can be separated as described above.

Compounds with the arrangement of Formula IV are obtained by a number of steps based on 2-[$(R^1,R^2)$-phenyl]-triazole-4-aldehydes (see Organic Synthesis Coll., Vol. B, p 429 [1955]; and K. Ogura et al., Tet. Letters, 15: 1383 [1972]):

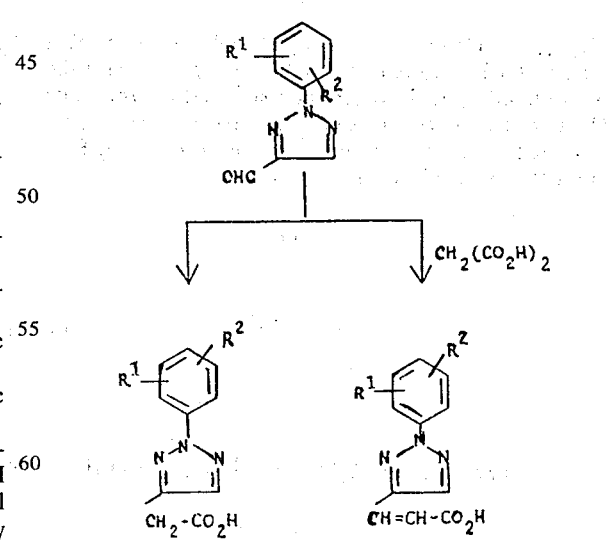

Compounds with the configuration of Formula VII can be prepared by the addition of $(R^1,R^2)$-phenylazides on acetylenic $R^4$-acids (E. Mugnaini et al., Atti. Accad. Nazl. Lincic., 14: 275 [1953]):

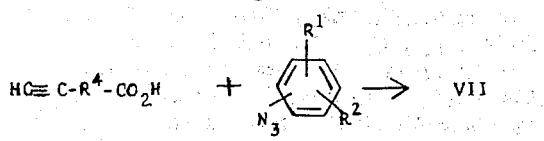

Compounds with the configuration of Formulas VIII thru X are prepared by the following general method:

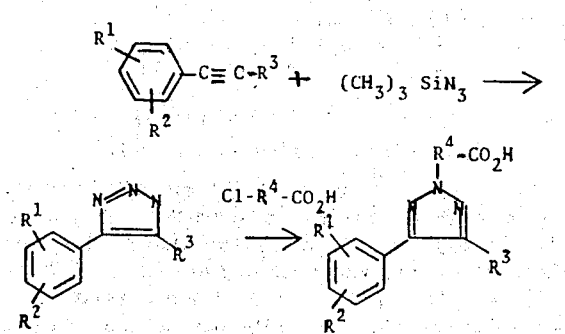

The phenyl- and (substituted)-phenyl-1,2,3,-triazole-alkanoic acid and -alkenoic acids represented by Formula I exhibit antiinflammatory activity in the adjuvant arthritis (a modification of the method described in J. Pharmacol. Exptl. Therap., 178: 223, [1971]) or the pleural effusion (reported in Soc. Exptl. Biol. Med., 127: 597 [1963]) model of inflammation in the rat. The antiinflammatory activity of some of the compounds of this invention is listed in Table 2 as the value R/E, the ratio of the activity of the reference drug (R), phenyl-butazone, to that of the compound tested (E). In Table 2, the compounds are identified by the number preceding each in the above list of preferred embodiments of Formula I. The symbols AA and PE signify the adjuvant arthritis and pleural effusion models of inflammation respectively.

Certain compounds having Formula I also exhibit antipyretic activity when tested in rats at a dose of 100 mg/kg according to the method in Tox. Appl. Pharmacology, 22: 672 (1972).

Table II

| Compound | R/E | | Anti-Pyretic (a) Activity |
|---|---|---|---|
| | AA | PE | |
| 2 | 0.81 | — | Yes |
| 3 | — | 3.02 | — |
| 5 | 1.03 | — | — |
| 6 | — | 2.08 | — |
| 7 | 0.79 | — | — |
| 9 | — | 1.28 | Yes |
| 10 | — | 1.17 | Yes |
| 11 | 0.88 | — | — |
| 12 | 1.54 | — | Yes |
| 13 | 1.27 | — | Yes |
| 15 | 2.39 | — | — |
| 19 | 3.93 | — | — |
| 21 | — | 3.84 | — |
| 26 | — | 3.89 | — |
| 28 | 4.33 | — | — |
| 29 | — | 4.29 | — |
| 34 | — | 1.91 | — |
| 35 | 1.15 | — | — |

(a) Tested at a dose of 100 mg/kg according to the method described in Tox. Appl. Pharmacol., 22: 672 (1972).

DESCRIPTION OF THE PREFERRED EMBODIMENTS

EXAMPLES 1–8

The following Examples have the configuration of Formula III, described in the SUMMARY OF THE INVENTION:

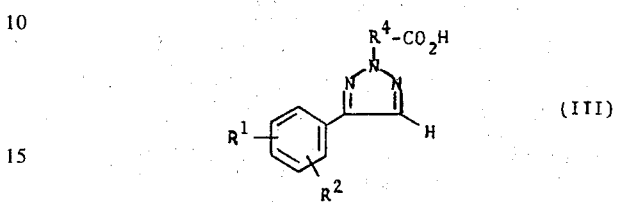

3-[4-Phenyl-1,2,3,(2H)-Triazole-2-Propionic Acid:

$R^1$ = H, $R^2$ = H, $R^4$ = —CH$_2$—CH$_2$—.

A solution of 40 g (0.28 moles) of 4-phenyltriazole, 31 g (0.28 moles) of β-chloropropionic acid, and 22.4 g (0.56 moles) of sodium hydroxide in 300 ml of water was refluxed for three days. Unreacted triazole was removed by precipitation with carbon dioxide and the cold filtrate acidified with 5N HCl. The precipitate was three times recrystallized from isopropanol to give 10 g of fine white needles, m.p. 139°–143°C.

Calculated for $C_{11}H_{11}N_3O_2$: C, 60.82; H, 5.11; N, 19.35; Found: C, 60.07; H, 4.86; N, 19.21

[4-Phenyl-1,2,3,(2H)-Triazole-2]-Acetic Acid:

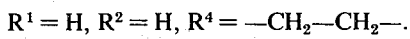

To a solution of 5 g (0.22 g-atm) of sodium in 500 ml of methanol was added 29 g (0.2 mole) of 4-phenyl-1,2,3 triazole followed by 24 g (0.22 mole) of methyl chloroacetate. After six hours reflux, the solvent was evaporated and the oily residue chromatographed on silica gel and eluted with chloroform. The fast moving material was collected and hydrolyzed by refluxing with HCl/acetic acid to give the 7 g of the desired acid, m.p. 199°C, after recrystallization from aqueous methanol.

Calculated for $C_{10}H_9N_3O_2$: C, 59.10; H, 4.46; N, 20.68; Found: C, 59.00; H, 4.50; N, 20.88

The following compounds were similarly prepared:

3-[4-(m-Acetamido)-Phenyl)-1,2,3,(2H)-Triazole-2]-Propionic Acid:

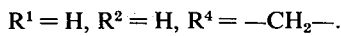

A solution of 9.5 g (0.036 moles) of 3-[4-(3-nitrophenyl)-1,2,3,(2H)-triazole-2]-propionic acid in 250 ml of ethanol was hydrogenated by standard methods. The crude amine was acetylated with acetic anhydride/pyridine. Recrystallization from acetone gave 5 g (45%) of an offwhite solid, m.p. 189°–191°C.

Calculated for $C_{13}H_{14}N_4O_3$: C, 56.92; H, 5.15; N, 20.48; Found: C, 56.86; H, 5.14; N, 21.18

3-[4-(m-Chloro)-Phenyl)-1,2,3,(2H)-Triazole-2]-Propionic Acid:

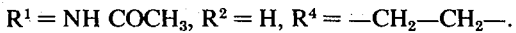

Calculated for $C_{11}H_{10}ClN_3O_2$: C, 52.70; H, 4.00; N, 16.71; Found: C, 52.34; H, 3.86; N, 16.66

4-[4-Phenyl-1,2,3,(2H)-Triazole-2]-Butyric Acid:

$R^1$ = H, $R^2$ = H, $R^4$ = —CH$_2$—CH$_2$—CH2—; M.P. 98°–99°C.

Calculated for $C_{12}H_{13}N_3O_2$: C, 62.32; H, 5.66; N, 18.18; Found: C, 62.47; H, 5.84; N, 18.35

4-[4-(m-Bromo)Phenyl-1,2,3,(2H)-Triazole-2]-Propionic Acid:

$R^1$ = Br, $R^2$ = H, $R^4$ = —CH$_2$—Ch$_2$—; M.P. 90°C.

Calculated for $C_{11}H_{10}BrN_3O_2$: C, 44.61; H, 3.40; N, 14.19; Found: C, 44.16; H, 3.31; N, 14.10

4-[4-(m-Methyl)Phenyl-1,2,3,(2H)-Triazole-2]-Propionic Acid:

$R^1$ = —CH$_3$, $R^2$ = H, $R^4$ = —CH$_2$—CH$_2$—; M.P. 93°C.

Calculated for $C_{12}H_{13}N_3O_2$: C, 62.32; H, 5.67; N, 18.18; Found: C, 62.29; H, 5.79; N, 18.29

4-[4-(3,5-Dichloro)Phenyl-1,2,3,(2H)-Triazole-2]-Propionic Acid:

$R^1$ = Cl, $R^2$ = Cl, $R^4$ = —CH$_2$—CH$_2$—; M.P. 122°–123°C.

Calculated for $C_{11}H_9Cl_2N_3O_2$: C, 46.17; H, 3.17; N, 14.69; Found: C, 46.10; H, 2.88; N, 14.71

EXAMPLES 9–14

Examples 9–14 have the molecular arrangement of Formula IV, disclosed in the SUMMARY OF THE INVENTION:

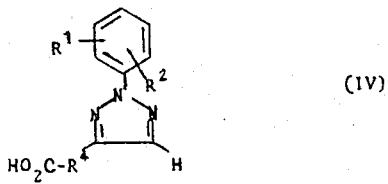

(IV)

3-[2-(3-Chlorophenyl)-1,2,3,(2H)-Triazole-4]-Acrylic Acid:

$R^1$ = Cl(meta), $R^2$ = H, $R^4$ = —CH=CH—.

Pure m-chlorophenylhydrazine hydrochloride, 100 g (0.44 moles) was converted to the free base and added to a solution of 36 g (0.2 moles) of fructose in 75 ml glacial acetic acid and 200 ml of water. The solution was heated to 60°C for four hours under N$_2$, then cooled and filtered. This gave the m-chlorophenylosazone of fructose as a yellow solid which was immediately dissolved in 600 ml of hot dioxane and added to a hot solution of 130 g (0.5 moles) of copper sulfate pentahydrate. After one hour at reflux, the black solution was cooled and the dark precipitate recrystallized from methanol with charcoal treatment. This gave 6 g of m-chlorophenylosotriazole as fine white needles, m.p., 196°–197°C.

A portion of this osotriazole, 1.86 g (0.0062 moles), was added to a solution of 5.7 g (0.025 moles) of periodic acid in 100 ml of water. After 16 hours, the solution was evaporated to near dryness and the residue diluted with 200 ml of water. The white precipitate was recrystallized from pentane to give 0.9 g of 2-(3-chlorophenyl)-1,2,3,(2H)-triazole-4carboxaldehyde as fine white needles, M.P., 89°C.

Calculated for $C_9H_6N_3ClO$: C, 52.06; H, 2.91; N, 20.24; Found: C, 51.97; H, 2.82; N, 19.90

Material from several runs was combined to give 8 g (0.039 moles) of aldehyde which was heated for two hours with 7.8 g (0.078 moles) of malonic acid and 20 ml of pyridine containing 1 ml of piperidine. After cooling, the solution was diluted with 500 ml of cold LNHCl and the precipitate collected and dried. Recrystallization from ethanol gave 7.3 g of the desired acrylic acid as white needles, M.P., 183°C.

Calculated for $C_{11}H_8N_3ClO_2$: C, 52.92; N, 3.23; N, 16.83; Found: C, 53.18; H, 3.16; N, 17.05

3-[2-Phenyl-1,2,3,(2H)-Triazole-4]-Propionic Acid:

$R^1$ = H, $R^2$ = H, $R^4$ = —CH$_2$—CH$_2$—.

The grams (0.047 moles) of 3-[2-phenyl-1,2,3(2H)-triazole-4]acrylic acid was hydrogenated at 50 psi over Raney nickle catalyst at room temperature. Recrystallizaion from benzene-heptane gave 7.8 g (77%) of white needles, m.p. 76°C. The starting material is a known compound (J. L. Riebsomer and G. Sumrell, J. Org. Chem. 13: 807 [1948]).

Calculated for $C_{11}H_{11}N_3O_2$: C, 60.82; N, 19.35; H, 5.11; Found: C, 61.22; N, 19.73; H, 5.22

The following were prepared by a similar synthesis:

3-[2-Phenyl-1,2,3,(2H)-Triazole-4]-Acrylic Acid:

$R^1$ = H, $R^2$ = H, $R^4$ = —CH=CH—; M.P., 180°–181°C.

Calculated for $C_{11}H_9N_3O_2$: C, 61.39; N, 19.53; H, 4.21; Found: C, 61.44; N, 19.88; H, 4.20

3-[2-(m-Chlorophenyl)-1,2,3,(2H)-Triazole-4]-Acrylic Acid:

$R^1$ = Cl(meta), $R^2$ = H, $R^4$ = —CH=CH—; M.P., 183°C.

Calculated for $C_{11}H_8ClN_3O_2$: C, 52.92; N, 16.83; H, 3.23; Found: C, 53.18; N, 17.05; H, 3.16

3-[2-(m-Bromo)Phenyl-1,2,3,(2H)-triazole-4]-Propionic Acid $R^1$ = Br, $R^2$ = H, $R^4$ = —CH$_2$—CH$_2$—; M.P., 96°–97°C.

Calculated for $C_{11}H_{10}BrN_3O_2$: C, 44.61; H, 3.40; 14.19; Found: C, 44.33; H, 3.33; 14.23

3-[2-(m-Bromo)Phenyl-1,2,3,(2H)-Triazole-4]-Acrylic Acid:

$R^1$=Br; $R^2$ = H, $R^4$ = —CH=CH—; M.P. 229°C.

Calculated for $C_{11}H_8BrN_3O_2$: C, 44.92; H, 2.74; N, 14.29; Found: C, 45.06; H, 2.72; N, 14.05

EXAMPLES 15–26

Examples 15–26 have the configurations of Formulas V and VI, described in the SUMMARY OF THE INVENTION:

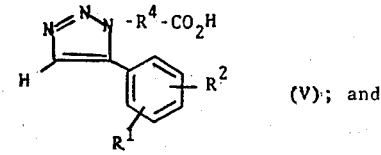

(V); and

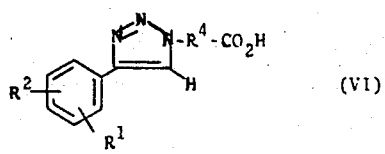

(VI)

A. 3-[5-Phenyl-1,2,3,(1H)-Triazole-1]-Propionic Acid (Formula V): $R^1 = H$, $R^2 = -CH_2-CH_2-$;

B. 3-[4-Phenyl-1,2,3,(1H)-Triazole-1]-Propionic Acid (Formula VII): $R^1 = H$, $R^2 = -CH_2-CH_2-$.

A. A solution of 35 g (0.34 moles) of phenylacetylene and 44 g (0.34 moles) of methyl β-azidopropionate in 100 ml of toluene were refluxed 16 hours. Upon cooling, 33 g of a crystalline product separated, m.p., 112°–115°C. Evaporation of the mother liquor gave 35 g of an amber oil.

The amber oil was refluxed one hour in a solution of 11 g NaOH in 175 ml of 60% aqueous methanol. The product was precipitated with mineral acid and recrystallized twice from aqueous methanol to give 24 g of the type V acid as white crystals, m.p., 181°C.

Calculated for $C_{11}H_{11}N_3O_2$: C, 60.82; H, 5.11; N, 19.35; Found: C, 60.84; H, 5.05; N, 19.93

B. The crystalline ester was hydrolyzed in like manner to give the type VII acid. After three recrystallizations from methanol-benzene this amounted to 6.5 g, m.p., 141°C.

Calculated for $C_{11}H_{11}N_3O_2$: C, 60.82; H, 5.11; N, 19.35; Found: C, 60.56; H, 5.09; N, 19.98

3-[4-(3-Acetamido)Phenyl-1,2,3,(1H)-Triazole-1]-Propionic Acid:

$R^1 = CH_3CONH$, $R^2 = H$, $R^4 = -CH_2-CH_2$.

3-[4-(3Nitrophenyl)-1,2,3,(1H)-triazole-1]-propionic acid was esterified with isopropanol to give 34 g of isopropyl 3-[4-(3-nitrophenyl)-1,2,3,(1H)-triazole-1propionate, m.p. 112°C.

Calculated for $C_{14}H_{16}N_4O_4$: C, 55.25; H, 5.30; N, 18.41; Found: C, 55.06; H, 5.18; N, 18.63

This ester (34 g, 0.11 mole) was hydrogenated in ethanol with Pd/C. An oil was obtained which was hydrolyzed directly by heating for 3 hours in 250 ml concentrated HCl. The acid solution was evaporated and the residue taken up in water. The free base was precipitated with sodium acetate. Recrystallization from aqueous ethanol gave 21 g of 3-[4-(3-aminophenyl)-1,2,3,(1H)-triazole-1]-propionic acid, m.p. 178°C.

Calculated for $C_{11}H_{12}N_4O_2$: C, 56.88; H, 5.21; N, 24.14; Found: C, 56.20; H, 5.25; N, 24.25

The above acid (11 g, 0.047 moles) was dissolved in 100 ml of hot glacial acetic acid containing 6.5 ml of acetic anhydride. After one hour, the reaction was cooled and filtered. Recrystallization from aqueous acetic acid gave 11.5 g of 3-[4-(3-acetamido-phenyl)-1,2,3,(1H)-triazole-1]-propionic acid, m.p. 237°C.

Calculated for $C_{13}H_{14}N_4O_3$: C, 56.92; H, 5.15; N, 20.48; Found: C, 56.54; H, 5.24; N, 20.50

The following compounds were synthesized in a similar fashion:

3-[5-(3-Fluoro)-Phenyl-1,2,3,(1H)-Triazole-1]Propionic Acid:

$R^1 = F(meta)$, $R^2 = H$, $R^4 = -CH_2-CH_2-$; M.P., 147°–148°C.

Calculated for $C_{11}H_{10}FN_3O_2$: C, 56.17; H, 4.29; N, 17.87; Found: C, 56.19; H, 4.29; N, 18.24

4-Phenyl-1,2,3,(1H)-Triazole-1-Acetic Acid:

$R^1 = H$, $R^2 = H$, $R^4 = -CH_2-$; M.P., 200°C.

Calculated for $C_{10}H_9N_3O_2$: C, 59.10; N, 20.68; H, 4.46; Found: C, 58.56; N, 20.71; H, 4.36

3-[4-(m-Chloro)-Phenyl-1,2,3,(1H)-Triazole-1]Propionic Acid:

$R^1 = Cl(meta)$, $R^2 = H$, $R^4 = -CH_2-CH_2-$; M.P., 173°–174°C.

Calculated for $C_{11}H_{10}ClN_3O_2$: C, 52.70; N, 16.71; H, 4.00; Found: C, 52.85; N, 16.84; H, 4.01

3-[4-(m-Bromo)-Phenyl-1,2,3,(1H)-Triazole-1]Propionic Acid:

$R^1 = Br(meta)$, $R^2 = H$, $R^4 = -CH_2-CH_2-$; M.P., 179°C.

Calculated for $C_{11}H_{10}BrN_3O_2$: C, 44.62; H, 3.40; N, 14.19; Found: C, 44.53; H, 3.38; N, 14.47

3-[4-(m-Fluoro)-Phenyl-1,2,3,(1H)-Triazole-1]Propionic Acid:

$R^1 = F(meta)$, $R^2 = H$, $R^4 = -CH_2-CH_2-$; M.P., 154°C.

Calculated for $C_{11}H_{10}FN_3O_2$: C, 56.17; H, 4.29; N, 17.87; Found: C, 56.38; H, 4.25; N, 18.08

3-[4-(m-Methyl)-Phenyl-1,2,3,(1H)-Triazole-1]Propionic Acid:

$R^1 = F(meta)$, $R^2 = H$, $R^4 = -CH_2-CH_2-$; M.P., 143°C.

Calculated for $C_{12}H_{13}N_3O_2$: C, 62.32; H, 5.67; N, 18.17; Found: C, 62.56; H, 5.71; N, 18.22

3-[4-(m-Ethoxy)-Phenyl-1,2,3,(1H)-Triazole-1]Propionic Acid:

$R^1 = OC_2H_5$, $R^2 = H$, $R^4 = -CH_2-CH_2-$; M.P., 138°C.

Calculated for $C_{13}H_{15}N_3O_3$: C, 59.76; H, 5.79; N, 16.08; Found: C, 59.37; H, 5.62; N, 16.40

3-[4-(m-Amino)-Phenyl-1,2,3,(1H)-Triazole-1]Propionic Acid:

$R^1 = -NH_2$, $R^2 = H$, $R^4 = -CH_2-CH_2-$; M.P., 177°–178°C.

Calculated for $C_{11}H_{12}N_4O_2$: C, 56.88; N, 24.14; H, 5.21; Found: C, 56.20; N, 24.25; H, 5.25

3-[4-Phenyl-1,2,3,(1H)-Triazole-1]Butyric Acid:

$R^1 = H$, $R^2 = -CH_2-CH_2-CH_2$; M.P. 136°C.

Calculated for $C_{12}H_{13}N_3O_2$: C, 62.32; H, 5.66; N, 18.18; Found: C, 62.47; H, 5.65; N, 18.40

EXAMPLES 27–31

The following examples have the configuration of Formula VII, described in the SUMMARY OF THE INVENTION:

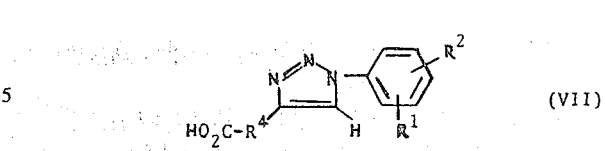

3-[1-Phenyl-1,2,3,(1H)-Triazole-4]Propionic Acid:

R¹ = H, R² = H, R⁴ = —CH₂—CH₂—.

A solution of 12 g (0.056 moles) of the above acrylic acid in 500 ml of dilute aqueous sodium bicarbonate was hydrogenated at room temperature with Raney nickel catalyst at 100 psi. After acidification, the product was recrystallized from aqueous ethanol to give 11 g of the desired propionic acid as white crystals, m.p., 138°C.

Calculated for $C_{11}H_{11}N_3O_2$: C, 60.82; H, 5.11; N, 19.35; Found: C, 61.01; H, 5.12; N, 19.84

The following compounds were similarly prepared:

3-[1-(m-Fluoro)-Phenyl-1,2,3,(1H)-Triazole-4]Propionic Acid:

R¹ = F(meta), R² = H, R⁴ = —CH₂—CH₂—; M.P., 134°C.

Calculated for $C_{11}H_{10}FN_3O_2$: C, 56.18; H, 4.29; N, 17.87; Found: C, 56.37; H, 4.30; N, 18.54

3-[1-(m-Chloro)-Phenyl-1,2,3,(1H)-Triazole-4]Propionic Acid:

R¹ = Cl(meta), R² = H, R⁴ = —CH₂—CH₂—; M.P., 166°C.

Calculated for $C_{11}H_{10}ClN_3O_2$: C, 52.49; H, 4.00; N, 16.70; Found: C, 52.24; H, 3.92; N, 17.42

3-[1-Phenyl-1,2,3,(1H)-Triazole-4]Acrylic Acid:

R¹ = H, R² = H, R⁴ = —CH=CH—

3-[1-Phenyl-1,2,3,(1H) triazole-4]acrolein, 31 (0.15 moles) was prepared and oxidized to the corresponding acrylic acid with basic silver oxide in water. After recrystallization from DMF-water this amounted to 12 g of white crystals, m.p., 279°C.

Calculated for $C_{11}H_9N_3O_2$: C, 61.40; H, 4.23; N, 19.53; Found: C, 60.22; H, 4.11; N, 19.48

The following compound was prepared in like fashion:

3-[1-(m-Fluoro)-Phenyl-1,2,3,)-Triazole-4]Acrylic Acid:

R¹ = F(meta), R² = H, R⁴ = —CH=CH—; M.P., 251°C.

Calculated for $C_{11}H_8FN_3O_2$: C, 56.65; H, 3.46; N, 18.02; Found: C, 56.25; H, 3.47; N, 18.62

EXAMPLES 32–34

Examples 32–34 are representative of Formula VIII, described in the SUMMARY OF THE INVENTION:

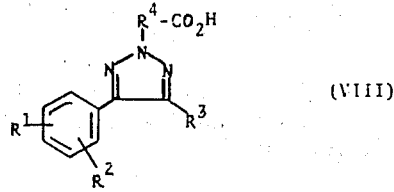

(VIII)

3-[4-Phenyl-5-Acetyl-1,2,3,(2H)-Triazole-2]Propionic Acid:

R¹ = H, R² = H, R³ = CH₃CO—; R⁴ = —CH₂—CH₂—.

A mixture of 30 g (0.21 mole) of acetylphenyl-acetylene and 24 g (0.21 mole) of trimethylsilyl azide was heated at 140°C for 24 hours. It was then cooled, dissolved in ether, and extracted with dilute sodium hydroxide. This aqueous layer was separated and made acidic with dilute HCl. The precipitate was recrystallized from benzene-petroleum ether to give 11 g (28%) of 4-acetyl-5-phenyltriazole, m.p. 117°–118°C.

This material was combined with 2 g from a previous run to give a total of 13 g (0.07 moles). It was dissolved in 200 ml of absolute methanol containing 1.9 g (0.083 g-atom) of sodium. The methanol was evaporated and the residue taken up in 150 ml of dimethylformamide, cooled to 0°C, and 6 g (0.083 moles) of β-propiolactone was added. After stirring overnight at room temperature, the solution was concentrated, diluted with water and the acid precipitated with dilute HCl. Recrystallization from petroleum ether gave 5 g (30%) of the desired acid, M.P., 110°–113°C.

Calculated for $C_{13}H_{12}N_3O_2$: C, 60.46; H, 4.68; N, 16.27; Found: C, 60.63; H, 5.11; N, 16.54

The following compounds were synthesized by a similar pathway:

3-[4-Phenyl-5-methyl-1,2,3,(2H)-Triazole-2]-Propionic Acid:

R¹ = H, R² = H, R³ = —CH₃, R⁴ = —CH₂—CH₂—; M.P., 114°–115°C.

Calculated for $C_{12}H_{13}N_3O_2$: C, 62.32; H, 5.66; N, 18.18; Found: C, 62.24; H, 5.54; N, 18.52

3-[4,5-Diphenyl-1,2,3,(2H)-Triazole-2]-Propionic Acid:

R¹ = H, R² = H, R³ = phenyl, R⁴ = —CH₂—CH₂—; M.P., 165°–166°C.

Calculated for $C_{17}H_{15}N_3O_2$: C, 69.61; H, 5.15; N, 14.33; Found: C, 69.11; H, 4.92; N, 14.29

EXAMPLE 35

This example is a preferred embodiment of Formulas IX and X, described in the above SUMMARY OF THE INVENTION:

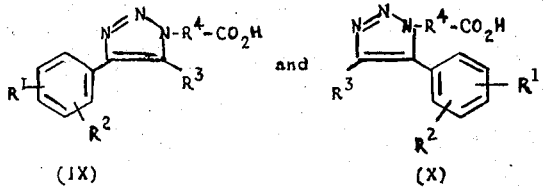

(IX) and (X)

3-[4,5-Diphenyl-1,2,3,(1H)-triazole-1]Propionic Acid:

R¹ = H, R² = H, R³ = phenyl, R⁴ = —CH₂—CH₂—.

A mixture of 50 g (0.28 moles) of diphenylacetylene and 33 g (0.28 moles) of trimethylsilylazide was heated at 150°C for several days. The cooled reaction mixture was extracted with hot dilute NaOH. This was washed with toluene while still warm, cooled, and acidified. The precipitate was recrystallized from toluene to give 17 g of 4,5-diphenyl-1,2,3(1H)-triazole, m.p. 131°C.

Material from several runs was combined to give 41.5 g (0.19 moles). This was dissolved in 400 ml of water at 80°C containing 7.5 g (0.19 moles) sodium hydroxide, and to the solution was added 20.5 g (0.19 moles) of 3-chloropropionic acid and 7.5 g (0.19 moles) of NaOH in an additional 250 ml water. After 18 hours at 80°C, the solution was cooled and acidified. A sticky precipitate formed which was taken up in ether and extracted with sodium bicarbonate solution. Acidification gave 36.5 g of crude acid which was esterified with a boron trifluoride-methanol complex and chromatographed on silica gel. This gave 21 g of methyl 3-[4,5-diphenyl-1,2,3,(2H)triazole-2]-propionate.

Hydrolysis in dilute hydrochloric acid gave, after recrystallization from aqueous methanol, 11 g of the desired acid, m.p., 165°–166°C.

Calculated for $C_{17}H_{15}N_3O_2$: C, 69.61; H, 5.15; N, 14.33; Found: C, 69.11; H, 4.92; N, 14.29

What is claimed is:

1. A compound having the formula

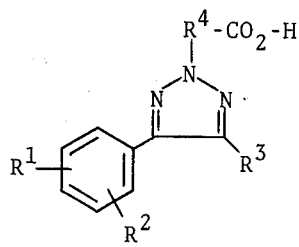

wherein:

$R^1$ is selected from the group consisting of: hydrogen, methyl, acetamido, and halogeno when $R^2$ is hydrogen; and chloro when $R^2$ is chloro;

$R^3$ is selected from the group consisting of hydrogen, acetyl, methyl, and phenyl; and $R^4$ is selected from the group consisting of —$CH_2$—, —$CH_2$—$CH_2$—, and —$CH_2$—$CH_2$—$CH_2$— radicals.

2. A compound as in claim 1, [4-phenyl-1,2,3,(2H)-triazole-2]-acetic acid.

3. A compound as in claim 1, 3-[4-phenyl-1,2,3,(2H)triazole-2]-propionic acid.

4. A compound as in claim 1, 3-[4-(m-chlorophenyl)-1,2,3,(2H)triazole-2]-propionic acid.

5. A compound as in claim 1, 3-[4-(m-acetamidophenyl)-1,2,3,(2H)-triazole-2]-propionic acid.

6. A compound as in claim 1, 4-[4-phenyl-1,2,3,(2H)-triazole-2]-butyric acid.

7. A compound as in claim 1, 3-[4-(m-bromo)-phenyl-1,2,3,(2H)-triazole-2]-propionic acid.

8. A compound as in claim 1, 3-[4-(m-methyl)-phenyl-1,2,3,(2H)-triazole-2]-propionic acid.

9. A compound as in claim 1, 3-[4-(3,5-dichloro)-phenyl-1,2,3,(2H)-triazole-2]-propionic acid.

10. A compound as in claim 1, 3-[5-methyl-4-phenyl-1,2,3,(1H)-triazole-2]-propionic acid.

11. A compound as in claim 1, 3-[4-phenyl-5-acetyl-1,2,3,(1H)-triazole-2]-propionic acid.

12. A compound as in claim 1, 3-[4,5-diphenyl-1,2,3,(1H)-triazole-2]-propionic acid.

* * * * *

UNITED STATES PATENT AND TRADEMARK OFFICE
CERTIFICATE OF CORRECTION

PATENT NO. : 3,948,932
DATED : April 6, 1976
INVENTOR(S) : Robert Thomas Buckler, Harold Eugene Hartzler, Shin Hayao, and Gust Nichols It is certified that error appears in the above—identified patent and that said Letters Patent are hereby corrected as shown below:

In column 1, line 46, delete "acid" (first occurrence) and instead insert -- or --.

In column 1, line 47, before $R^4-CO_2H$, insert -- - -- (hyphen).

In column 3, line 9, insert -- - -- (hyphen) between "(2H)" and "triazole".

In column 3, line 61, delete "t" (first occurrence) in "tthrough".

In column 5, line 26, delete "acid" (first occurrence).

In column 7, line 67, insert -- - -- (hyphen) between "4" and "carboxaldehyde".

In column 8, line 1, delete "C9H6N3C10", and instead insert -- $C_9H_6N_3Cl0$ --.

In column 8, line 9, delete "LNHCl", and instead insert -- 1NHCl --.

In column 9, line 34, insert -- ] -- after "1".

Signed and Sealed this

Twenty-fourth Day of January 1978

[SEAL]

Attest:

RUTH C. MASON
Attesting Officer

LUTRELLE F. PARKER
Acting Commissioner of Patents and Trademarks